US00PP08417P

United States Patent [19]

Jessel, Jr.

[11] Patent Number: Plant 8,417

[45] Date of Patent: Oct. 12, 1993

[54] CARNATION PLANT NAMED CFPC FESTIVE

[75] Inventor: Walter H. Jessel, Jr., Salinas, Calif.

[73] Assignee: California Florida Plant Co., L.P., Salinas, Calif.

[21] Appl. No.: 950,304

[22] Filed: Sep. 24, 1992

[51] Int. Cl.[5] ..... A01H 5/00

[52] U.S. Cl. ..... Plt./70.2

[58] Field of Search ..... Plt./70.1, 70.2, 70.4

*Primary Examiner*—Howard J. Locker

*Attorney, Agent, or Firm*—Christie, Parker & Hale

[57] ABSTRACT

A new carnation of light yellow picotee red coloration.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation. The varietal denomination of this new carnation is 'CFPC Festive'.

Among the novel combination of characteristics possessed by the new variety which distinguishes it are flowers of the attractive light yellow picotee red flower coloring which are produced on strong stems.

The new variety was developed to produce a variety that corrects shortcomings of two varieties no longer available, 'Lek's Kissi' and 'Hilfas', which had too tall a habit and late response. The new variety has a fast flowering response of 3½ months from a mid-April planting, which is 1½ months earlier than 'Hilfas' according to prior data. It is also shorter and has improved spray formation than 'Hilfas' which also had a rather wild growth and spray.

Asexual reproduction by propagation by side shoot cuttings of the new variety as performed in Fremont and Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Festive'.

BRIEF DESCRIPTION OF THE ILLUSTRATION

The accompanying illustration shows typical specimens of the vegetative growth and flowers in different stages of development of the new variety depicted in color as nearly true as it is reasonably possible to make the same in a color illustration of this character.

DESCRIPTION OF THE NEW VARIETY

The following is a detailed description of my new variety, with color terminology in accordance with the Royal Horticultural Society Colour Chart (RHSCC). The terminology used in the color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont, Calif. The height of plant and flower and foliage size are established as an average using standard commercial cultural practices.

Name: 'CFPC Festive'.

Classification:

*Botanical.*—*Dianthus caryophyllus.*

*Commercial.*—Carnation, spray type.

Parentage:

*Female parent.*—Unnamed seedling (No. 870705).

*Male parent.*—Unnamed seedling (No. 870647).

Plant:

*Height.*—About 27 inches, (first flowering).

*Growing habit.*—Herbaceous, semi-upright.

*Blooming habit.*—Terminal as a spray.

*Blooming season.*—Year round.

*Rooting time.*—About 15–16 days.

*Mutation prone.*—Does not appear to be.

*Disease resistance.*—Unknown.

*Temperature tolerance.*—Typical for carnation.

*Breaking action.*—Good.

Foliage:

*Color.*—Upper side: Near 141D. Lower side: Near 141B.

*Size.*—About 3 inches long at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About 1-inch.

*Diameter.*—About ½-inch.

Calyx:

*Number of sepals.*—About 5.

*Length.*—About ¾-inch.

*Width.*—About ⅜-inch.

*Color.*—Outside — Near 143A. Inside — Near 144D.

Bloom:

*Shape.*—Round.

*Size.*—Diameter average: About 1½ inches. Depth average: About 1 inch.

*Borne.*—Terminal as a spray.

*Color.*—General tonality: Light yellow picotee red (near 51A-51B faded). Upper side: Near to from 2C to 11D (faded). Lower side: Near to from 2D to 11D. Center: Near to from 2C to 11D.

*Keeping quality.*—Good.

*Fragrance.*—Slight.

Petals:

*Number.*—About 32.

*Outer petals.*—Length: About 1-inch. Width: About ½-inch.

*Central petals.*—Length: About ½-inch. Width: About ⅓-inch.

*Texture.*—Smooth.

*Form.*—Fan shaped.

*Appearance.*—Shiny.

Reproductive organs:

*Stamens.*—Number: About 11. Arrangement: Around the ovary.

*Anthers.*—Length: About 1/10-inch. Color: Near 160A.

*Filaments.*—Length: About 1-inch. Color: Near 155A.

*Pistil.*—Number: About 2. Color: Near 4D.

*Stigma.*—Number: About 2. Color: Near 4D.

*Ovary.*—Shape: Conical, ribbed. Color: Base — Green. Body — Green. Apex — Tan.

*Fertility.*—Male — Fair. Female — Fair.

I claim:

1. A new and distinct variety of carnation plant, substantially as shown and described.

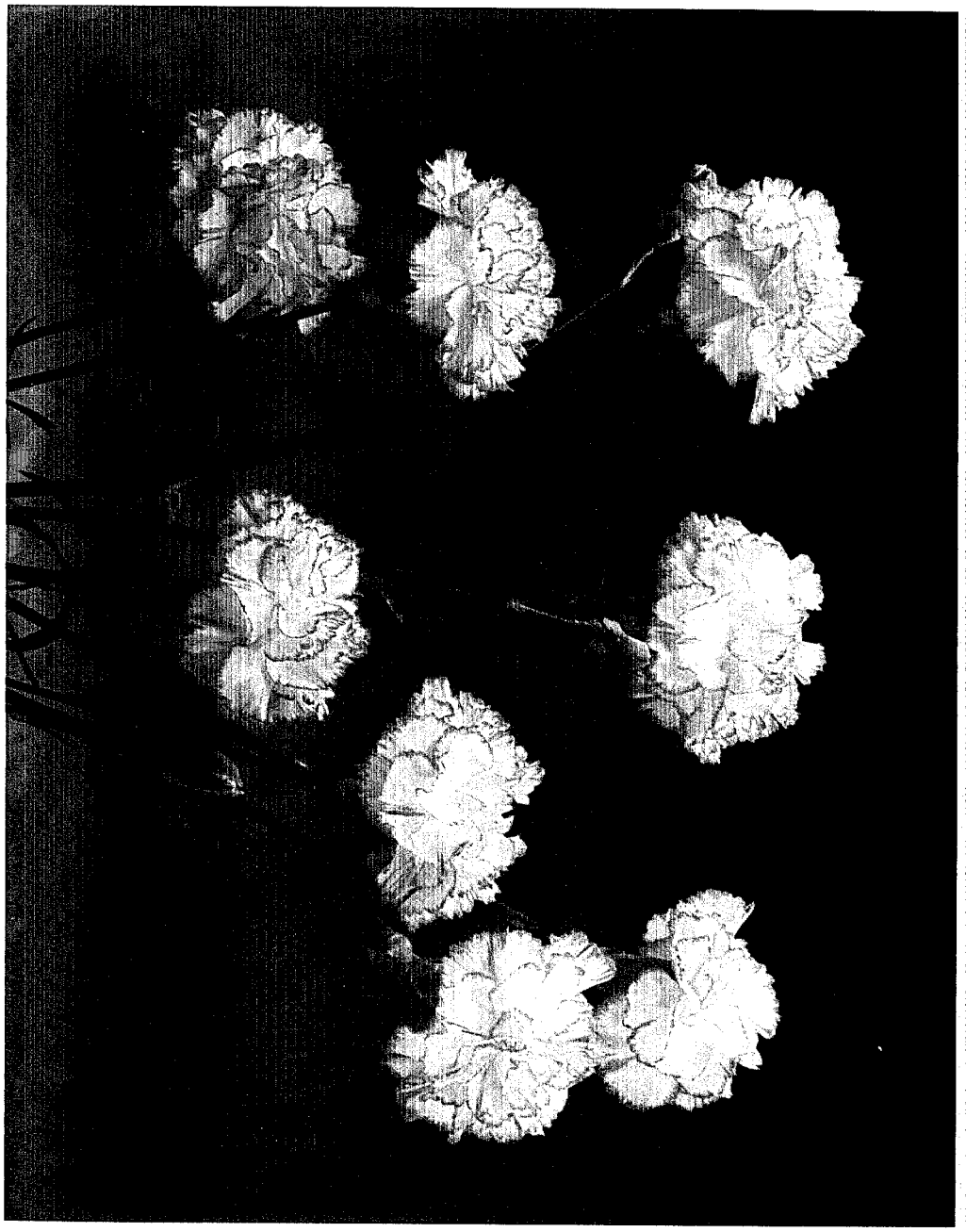

* * * * *